(12) United States Patent
Huang et al.

(10) Patent No.: US 7,351,710 B2
(45) Date of Patent: Apr. 1, 2008

(54) PREPARATION OF AMORPHOUS FORM OF INDIPLON

(75) Inventors: Le Huang, Shang Gao County (CN); Hui Min He Huang, Northborough, MA (US)

(73) Assignee: Mai De Ltd., Northborough, MA (US)

( * ) Notice: Subject to any disclaimer, the term of this patent is extended or adjusted under 35 U.S.C. 154(b) by 0 days.

(21) Appl. No.: 11/347,753

(22) Filed: Feb. 6, 2006

(65) Prior Publication Data

US 2006/0189633 A1    Aug. 24, 2006

(30) Foreign Application Priority Data

Feb. 18, 2005    (CN) .................. 2005 1 0033218

(51) Int. Cl.
*A61K 31/519* (2006.01)
*C07D 487/04* (2006.01)
*A61P 25/20* (2006.01)

(52) U.S. Cl. .................... 514/259.3; 544/281
(58) Field of Classification Search ................ 544/281; 514/259.3
See application file for complete search history.

(56) References Cited

U.S. PATENT DOCUMENTS

| | | | |
|---|---|---|---|
| 4,521,422 A | 6/1985 | Dusza et al. | |
| 6,384,221 B1 | 5/2002 | Thiele et al. | |
| 6,399,621 B1 | 6/2002 | Dusza et al. | |
| 6,472,528 B1 * | 10/2002 | Gross et al. | ................ 544/281 |
| 6,544,999 B2 | 4/2003 | Thiele et al. | |
| 6,903,106 B2 * | 6/2005 | Zook et al. | .............. 514/259.3 |
| 6,958,342 B2 * | 10/2005 | Thiele et al. | ............ 514/259.3 |
| 2004/0116446 A1 | 6/2004 | Zook et al. | |

OTHER PUBLICATIONS

Merck Index, 12th edition, p. 7733.*
Lactel—Chemical and Physical Properties, <http://www.absorbables.com/properties.htm> downloaded Sep. 12, 2007.*
Telko et. al. (Respiratory Care, 2005 50(9), 1209-1227.*

* cited by examiner

*Primary Examiner*—Brenda L. Coleman
*Assistant Examiner*—Susanna Moore

(57) ABSTRACT

The present invention is directed to amorphous form of indiplon, to processes for preparing said amorphous form, to pharmaceutical compositions containing the same, and to method of treatment using the same. Additionally, the present invention also relates to the preparation of solid amorphous dispersion of indiplon and a carrier which includes PVP and solid PEG etc.

13 Claims, 1 Drawing Sheet

PREPARATION OF AMORPHOUS FORM OF INDIPLON

FIELD OF THE INVENTION

Figure 1:
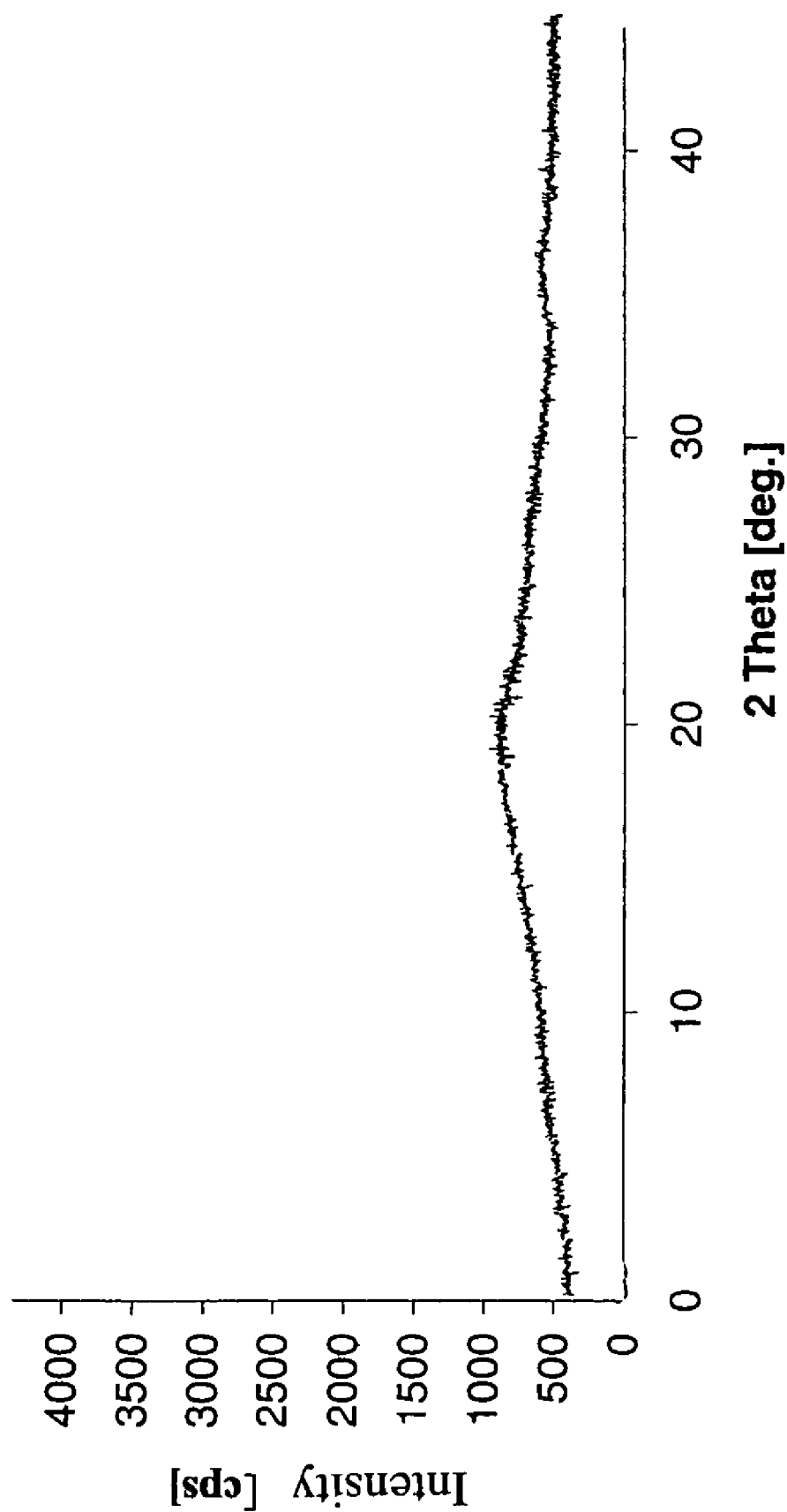

The present invention is directed to amorphous form of indiplon, to processes for preparing said amorphous form, to pharmaceutical compositions containing the same, and to method of treatment using the same.

BACKGROUND OF THE INVENTION

Indiplon is the common chemical name of N-Methyl-N-[3-[3-[2-thienylcarbonyl]pyrazolo[1,5-a]pyrimidin-7-yl]phenyl]acetamide, and its chemical structure is shown as follows:

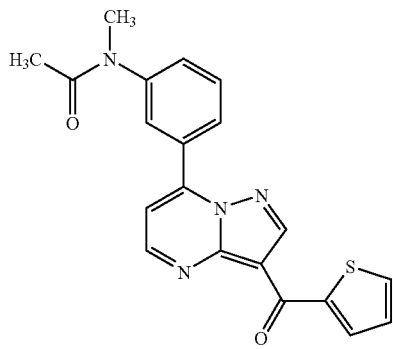

Indiplon is a safe and effective drug for the treatment of insomnia or chronic insomnia, and it is a high-affinity allosteric potentiator of GABAA responses. U.S. Pat. No. 4,521,422 discloses the preparation of indiplon and its derivatives and their uses as anxiolytic, anticonvulsant, sedative-hypnotic and skeletal muscle relaxant agents. In U.S. Pat. No. 6,399,621, the use of indiplon for the prevention and treatment of insomnia, particularly for chronic insomnia is disclosed. Crystalline indiplon was obtained according to the procedures described in above references. Details for preparation of crystalline indiplon were described in Example 1 of U.S. Pat. No. 4,521,422 and examples of U.S. Pat. No. 6,399,621. Example 1 of U.S. Pat. No. 4,521,422 has a following statement: "a reaction mixture of 3-amino-1H-pyrazol-4-yl)phenyl-methanone and 3-dimethylamino-1-(3-pyridinyl)-2-propen-1-one in 25 mL of glacial acetic acid was refluxed for 6 hours and then the solvent was removed in vacuums giving a crystalline residue. This residue was partitioned between saturated aqueous sodium bicarbonate and dichloromethane. The organic layer was dried with anhydrous sodium sulfate and then passed through a short pad of hydrous magnesium silicate. The addition of hexane to the refluxing eluate induced crystallization". The obtained substance is subsequently confirmed as a mixture of crystalline Form-I and Form-II of indiplon, as described in Example 1 of U.S. Pat. No. 6,384,221.

U.S. Pat. Nos. 6,384,221 and 6,544,999 disclose two crystalline forms (designated as Form I and II) of indiplon. Publication US 2004/0116446 further discloses a third polymorphic form (designated as Form III) of indiplon.

All of references cited above completely failed to describe or disclose amorphous form of indiplon.

Recently, the difference in many aspects of solid-state properties such as solubility, dissolution and bioavailability of crystal (polymorphic) forms and amorphous forms of a given drug substance has been widely reported. Many drugs such as antibiotics, hypnotics, lipid and high blood pressure lowering agents display the ploymorphic forms, which include different physical state, crystalline state, liquid state and non-crystalline (amorphous) state.

It has been disclosed earlier that the amorphous forms in a number of drugs exhibit different dissolution characteristics and in some cases different bioavailability patterns compared to crystalline forms [Konne T., Chem Pharm Bull, 38, 2003 (1990)]. For some therapeutic indications one bioavailability pattern may be favored over another. An amorphous form of cefuroxime axietil is a good example for exhibiting much higher bioavailability than the crystalline forms, which leads to the selection of amorphous form as the final drug substance for cefuroxime axietil pharmaceutical dosage form development. Additionally, the aqueous solubility of crystalline atorvastatin calcium is lower than its amorphous form, which may result in the difference in their in vivo bioavailability.

Indiplon is a substance that is practically insoluble in water, and the solubility of crystalline indiplon is only 20-30 µg/ml. Therefore, there is a need to search for a more soluble form of indiplon, and amorphous form of indiplon may be particularly desirable. As solubility of amorphous form of indiplon in water increases, its dissolution rate may be faster and bioavailability may be higher than crystalline indiplon. We have now surprisingly and unexpectedly discovered that a new form of indiplon, e.g., pure amorphous form of indiplon can be prepared by simple and reproducible processes.

SUMMARY OF THE INVENTION

According to one aspect, the present invention provides an amorphous form of indiplon.

According to another aspect, the present invention provides a process for preparing the amorphous form of indiplon by using distillation technique.

According to a further aspect, the present invention provides a process to prepare the amorphous form of indiplon by using spray-drying technique.

According to another aspect, the present invention provides a solid amorphous dispersion of indiplon and a carrier. The said carrier is selected from a group of excipients including solid polyethylene glycol (PEG), polyvinylpyrrolidone (PVP), lactose, starches, manitol, methylcelluse, hydroxylmethylcelluse, ethylcelluse, hydroxyethylcelluse, hydroxylpropylcelluse, hydroxylpropylmethylcelluse (HPMC), α-cyclodextrin, β-cyclodextrin or hydroxylpropyl-β-cyclodextrin.

BRIEF DESCRIPTION OF THE ACCOMPANYING DRAWINGS

FIG. 1 is X-ray powder diffraction pattern of amorphous form of indiplon.

DETAILED DESCRIPTION OF THE INVENTION

According to one aspect, the present invention provides a new form of indiplon, e.g., amorphous form of N-Methyl-N-[3-[3-[2-thienylcarbonyl]pyrazolo[1,5-a]pyrimidin-7-yl]phenyl]acetamide (indiplon). The amorphous form of indiplon herein refers to a solid composition of indiplon that contains less than 5% crystalline indiplon, preferably contains less than 2% crystalline indiplon, more preferably contains less than 0.5% or essentially free of crystalline indiplon. The ratio of amorphous form to crystalline form is generally determined by X-ray powder diffraction pattern technique, as shown in the accompanied drawing of FIG. 1. Since the molecule arrangement of amorphous material is in a completely disorder state, the X-ray powder diffraction pattern of amorphous form does not show any discernible or sharp peaks that are characteristics of crystalline material, and only a broad curve is observed, thus demonstrating the amorphous nature of the product. The amorphous form of indiplon characterized by X-ray powder diffraction pattern is essentially identical to the accompanied drawing of FIG. 1 in the present invention.

According to another aspect, the present invention provides two processes for preparing amorphous form of N-Methyl-N-[3-[3-[2-thienylcarbonyl]pyrazolo[1,5-a]pyrimidin-7-yl]phenyl]acetamide (indiplon).

Accordingly, the first process for preparing amorphous indiplon is a distillation method under reduced pressure, including the following steps:

a) dissolving crystalline indiplon or a mixture of crystalline and amorphous indiplon in a solvent of dichloromethane, acetone, acetonitrile or in a straight or branched chain $C_1$-$C_4$ alcohol solvent, b) removing the solvent from the solution to obtain solid substance using distillation technique at reduced pressure, c) drying the solid product to obtain amorphous indiplon.

More specifically, the crude or pure crystalline or crystalline and amorphous mixtures of indiplon is dissolved in dichloromethane, acetone, acetonitrile or mixtures thereof, or in a straight or branched chain $C_1$-$C_4$ alcohol solvent (e.g. methanol or ethanol) at heating, with a concentration of 0.5% (w/v) to 30% (w/v), preferably with a concentration of 1% (w/v) to 15% (w/v). The solution is heated up under reflux, and the solvent is then removed from the solution to dryness under reduced pressure using distillation method, thereby leaving a solid residue. The reduced pressure is generally 400 mmHg or less, preferable less than 100 mmHg, most preferably 30-80 mmHg. The solvent residue is further removed by drying the product under vacuum oven to afford solid product. The obtained product may also be dried in a tray drier or in a fluid bed dryer. Preferably, the obtained product is dried under vacuum at 20-65° C., preferably at 35-45° C. For example, the product is dried in a tray drier preferably for 6-20 hours at 20-65° C., and most preferably for 15 hours at 35-45° C., to afford the amorphous form of indiplon.

The obtained product prepared according to the process of the present invention may be characterized by X-ray powder diffraction pattern, as shown in the accompanied drawing of FIG. 1. The X-ray powder diffraction pattern of pure amorphous form of indiplon obtained in the present invention does not show any discernible or sharp peaks that are characteristic of crystalline materials; only a flat or broad curve is observed, thus demonstrating the amorphous nature of the product.

It has been unexpectedly found that uniformed and pure amorphous form of indiplon can be obtained in simple and reproducible process as described above.

The straight or branched chain $C_1$-$C_4$ alcohol solvent in the present invention is selected from the group of methanol, ethanol, n-propanol, isopropanol or branched-chain butanols, preferably the alcohol solvent is methanol, ethanol or mixtures thereof. The processes can be carried out with two or more alcohol solvents.

According to a preferred aspect of the present invention, the process for preparation of amorphous form of indiplon can be carried out by using the solvent selected from group of dichloromethane, acetone, acetonitrile or mixtures thereof, and most preferably by using dichloromethane.

According to a preferred aspect, the present invention also provides a process for preparation of amorphous form of indiplon, including the following steps: the starting materials are dissolved in solvent at heating, preferably heating solvent to the boiling point. The solvent is then removed by distillation under reduced pressure (30-80 mmHg); the solid product is further dried under vacuum oven at 35-50° C. to afford amorphous form of indiplon.

According to a further aspect, the present invention provides another process to prepare amorphous form of indiplon by spray drying technique, including the following steps:

a) dissolving the starting material of crystalline or mixtures of crystalline and amorphous indiplon in acetone, dichloromethane, a straight or branched chain $C_1$-$C_4$ alcohol solvent or mixture thereof;

b) stirring and heat the resulting solution;

c) spray drying the solution to afford solid residue;

d) drying the product to obtain amorphous indiplon.

More specifically, the starting material indiplon is dissolved in acetone, dichloromethane, straight or branched chain $C_1$-$C_4$ alcohol solvent (e.g. methanol or ethanol) or mixtures thereof under heating (40-65° C.), with a concentration of 0.5% (w/v) to 30% (w/v), preferably with a concentration of 1.5% (w/v) to 15% (w/v). The solution is spray dried after it is cooled to 30° C. The spray drying process can be carried out using any commercially available spray dryers, which operates on the principle of nozzle spraying in a parallel flow. For instance, the sprayed product and drying gas flow in the same direction. The drying gas can be air or inert gasses such as nitrogen, argon and carbon dioxide. The use of nitrogen gas for inert gas is preferred in this invention. The spray drying in-let temperature is about 115-160° C., and the out-let temperature is about 55-90° C. at a feed rate of 2-30 mL/second. The solvent is removed from the solution by spray drying to afford solid residue. The obtained product may be further dried in a tray drier or in a fluid bed dryer or dried under vacuum oven to obtain a desirable amorphous product. For example, the obtained amorphous form of indiplon of the present invention is dried in a tray drier, preferably for 6-20 hours at 20-60° C., and most preferably for 12-20 hours at 35-45° C. The obtained product prepared according to the processes of the present invention may be characterized by X-ray powder diffraction pattern, as shown in the accompanied drawing of FIG. 1. The X-ray powder diffraction pattern of amorphous indiplon does not show any discernible peaks that are characteristic of crystalline materials; only a flat and broad curve line is observed, thus demonstrating the amorphous nature of the product.

It has been unexpectedly found that uniformed and pure amorphous form of indiplon can be obtained in simple and reproducible processes as described above.

The amorphous form of indiplon described in the present invention covers both anhydrous amorphous indiplon and amorphous indiplon hydrate.

According to the preparation process of the present invention, starting materials can be indiplon prepared according to any known procedures. Starting materials can be crude or pure indiplon, preferably indiplon with purity over 95%, most preferably with purity over 98%. Starting materials can be crystalline indiplon or mixtures of crystalline and amorphous indiplon. Crystalline indiplon includes Form I, Form II, Form III or mixtures of these three crystalline forms in any ratio, preferably starting materials is the indiplon prepared according to the procedures as described in U.S. Pat. No. 4,521,422. Polymorphic forms of indiplon can be prepared according to the procedures as described in patents U.S. Pat. Nos. 4,521,422, 6,399,621, 6,384,221 and 6,544,999) or their cited references therein.

Amorphous indiplon prepared according to the process of the present invention may be characterized by X-ray powder diffraction pattern, as shown in the accompanied drawing of FIG. 1. The X-ray powder diffraction pattern of amorphous indiplon does not show any discernible peaks that are characteristic of crystalline materials. The lack of discernible or sharp peaks indicates the characteristic feature of amorphous indiplon, and also demonstrating the amorphous nature of the obtained product.

The amorphous form of indiplon prepared according to the procedures of the present invention and pharmaceutically acceptable carrier can be used to make pharmaceutical compositions. Therefore, the present invention further provides a pharmaceutical composition for administering effective amount of amorphous form of indiplon as active ingredient in unit dosage forms. The unit dosage forms can be administered in a wide variety of oral and parenteral dosage forms, such as by injection, that is, intravenously or intramuscularly. Also, the amorphous form of indiplon of the present invention can be administered by inhalation, e.g. intranasally or transdermally. It will be obvious to those skilled in the art that the following dosage forms may comprise either amorphous form of indiplon, or a corresponding pharmaceutically acceptable salt of a compound of the present invention as the active component.

For preparing pharmaceutical compositions comprising amorphous form of indiplon, pharmaceutically acceptable excipients can be either solid or liquid.

Solid form of pharmaceutical compositions includes powders, tablets, pills, capsules, cachets, suppositories, and dispersible granules. A solid carrier can be one or more substances that may also act as diluents, flavoring agents, solubilizers, lubricants, suspending agents, binders, preservatives, tablet disintegrating agents, or an encapsulating material.

In powders, the excipient is a finely divided solid that is mixed with the finely divided active component. In tablets, the active component is mixed with the carrier having necessary binding properties in suitable proportions and compacted in the shape and size desired.

The powders and tablets preferably contain from one or ten to about seventy percent of the active compound. Suitable carriers are magnesium carbonate, magnesium stearate, talc, sugar or lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component, with or without other carriers, is surrounded by a carrier, which is thus in association with it. Similarly, tablets, powders, capsules, pills, cachets, and lozenges can be used as solid dosage forms suitable for oral administration.

Tablets can be made by compressing active ingredient powders or particles and a binder mixed with one or more excipients through a tablet compression machine. The suitable excipients are sodium hydroxylmethylcelluse, lubricants, inert excipients, preservatives and disintegrating agents (e.g., sodium starch glycolate, cross-polyvinylpyrrolidone, sodium methylcelluse carboxlate) or dispersion. Tablets can also be coated with suitable coating agents, and they may be immediate release or sustained release drug products.

For preparing suppositories, a low melting wax, such as a mixture of fatty acid glycerides or cocoa butter, is first melted and the active component is then dispersed homogeneously therein, as by stirring. The homogenous mixture is then poured into molds with suitable size, allowed to cool, and thereby to solidify.

The oral solution of the present invention can be solutions or suspensions, which is made using water or a mixture of water and propylene glycol. The injection solution can be made using polyethylene glycol (PEG). For example, this type of oral solution can be made with pharmaceutically acceptable carriers such as cellulose derivatives, edible lipids, emulsifiers, hydrophobic carriers and preservatives. The oral solution can also include color additives, sweetners and buffers.

The emulsified oral solution prepared with water can be manufactured by the following procedure: dissolving the active ingredient in water, and then adding a material with high viscosity, such as natural or synthetic gels, resins, methylcellulose, sodium hydroxymethylcellulose which are often used as emulsifiers.

The pharmaceutical composition of the present invention is preferably in unit dosage form. In such form, the preparation is subdivided into unit doses containing appropriate quantities of the active component. The unit dosage form can be a packaged preparation, and the package contains discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

In order to prevent amorphous state of indiplon from converting into crystalline state, a solid amorphous dispersion of indiplon and a carrier can be used to make said solid pharmaceutical compositions. Therefore, the present invention further provides a solid amorphous dispersion of indiplon and a carrier. For solid amorphous dispersion of indiplon, the composition contains less than 5% of the crystalline form of indiplon, preferably less than 2% the crystalline form of indiplon, most preferably less than 0.5% or substantially free of any crystalline forms other than its amorphous form. For the carrier in solid amorphous dispersion, the composition contains less than 5% of the crystalline form of carrier, preferably less than 2% crystalline form of carrier, most preferably less than 0.5% or substantially free of any crystalline form of carrier other than its amorphous form.

The solid amorphous dispersion of the present invention has the following characteristics. The amorphous indiplon is evenly dispersed in the amorphous carrier. This highly dispersed material does not contain any crystalline substance, and therefore, it will not induce the crystallization of amorphous material to become a crystalline material. That is, since the amorphous indiplon is highly dispersed in the amorphous carrier, it will not convert back into crystalline indiplon. The solid amorphous dispersion of indiplon is also stable, and has a good material flow property and high bulk & tap density, and thus it is particularly suitable for preparation of pharmaceutical composition.

The carrier used to make the solid amorphous dispersion of the present invention may be an amorphous material or it can be converted into amorphous material. The suitable carriers should be soluble in methanol, ethanol, acetonitrile, acetone and dichloromethane or mixtures thereof. The suitable carriers should be pharmaceutically acceptable as well. The carriers of the present invention include various types of polyethylene glycols (PEG), polyvinylpyrrlidones (PVP), sugars, lactose, starches, manitol, methylcellulose, hydroxylethylcellulose, hydroxylmethylcellulose, ethylcellulose, hydroxylpropylmethylcellulose (HPMC) or cyclydextrins. Preferred polyethylene glycols (PEG) are PEG 4000, PEG 5000, PEG 6000 or PEG 8000. Preferred polyvinylpyrrolidones (PVP) are PVP K15 or PVP K30.

Additional suitable carriers to make the solid amorphous dispersion of the present invention include α-cyclodextrin, β-cyclodextrin, hydroxylpropyl-β-cyclodextrin, preferably hydroxylpropyl-β-cyclodextrin. The suitable carriers to make the solid amorphous dispersion of the present invention should be commercially available or can be made by known procedures.

According to another aspect, the present invention provides a process for preparing a solid amorphous dispersion of indiplon and a carrier using distillation or spray drying technique, and the details can be found in examples of the present inventions. Distillation technique for preparing solid amorphous dispersion includes the following steps: dissolving the starting materials of indiplon in a solvent, e.g. methanol, ethanol, acetone, dichloromethane or mixtures thereof at heating, preferably heated to boiling point of the solvent; evaporating the solvent under the reduced pressure to dryness; grinding the solid residues; and drying the product under vacuum at 35-45° C. Spray drying technique for preparing solid amorphous dispersion comprises the following steps: dissolving the starting material of indiplon in a solvent, e.g. methanol, ethanol, acetone, dichloromethane or mixtures of solvents thereof at heating; cooling the solution to 30° C.; removing the solvent by spray drying to afford solid residues; drying the product under vacuum at 35-45° C. Alternatively, the indiplon and carrier solution can be prepared by separately dissolving indiplon or carrier in a solvent to give individual solution, and then indiplon solution can be added into the carrier solution or vice versa to afford a solution of indiplon and carrier.

The solid amorphous dispersion of indiplon and a carrier and pharmaceutically acceptable excipients can be used to prepare pharmaceutical compositions. Therefore, according to a further aspect, the present invention provides a pharmaceutical composition for administering effective amount of amorphous indiplon in a form of solid amorphous dispersion in unit dosage forms. The unit dosage forms can be administered in a wide variety of oral and parenteral dosage forms as described above. Additionally, it will be obvious to those skilled in the art that the following dosage forms may comprise either amorphous indiplon or a corresponding pharmaceutically acceptable salt of a compound of the present invention as the active component.

The suitable excipient in pharmaceutical composition may include anti-oxidants to stabilize the active ingredient, for example, to prevent the active ingredient from oxidative degradation. Similarly, the suitable excipient can also include surfactants such as sodium lauryl sulphate to enhance the dissolution rate of the active ingredient.

Amorphous indiplon in unit dosage form may comprise 1-200 mg, preferably 2-100 mg, most preferably 5-50 mg, as active ingredient.

The unit dosage forms of pharmaceutical composition comprising amorphous indiplon or its solid amorphous dispersions can be immediate release or sustained release products, and they can be prepared according to the conventional procedures used in pharmaceutical industry. The details for preparation of tablets and capsules are described in Example 3 of the present invention.

As mentioned previously, indiplon is a new generation of drug useful to the treatment of insomnia or chronicle insomnia. It is also a useful anxiolytic, anticonvulsant, sedative-hypnotic and skeletal muscle relaxant agent.

Though the present invention has described details of various embodiments, it will be obvious to those skilled in the art that similar situations, modifications or amendments should be included in the present invention as well. The following examples are provided to illustrate specific embodiments of the present invention, they are not intended to be limiting in any way.

EXAMPLES

Example 1

Preparation of Amorphous Indiplon and Solid Amorphous Dispersion: Distilling Method Method A: crystalline indiplon (5.0 g) was dissolved in acetone (50 ml) solvent under heating to 40° C. The solution was further heated to boiling point. The solvent was evaporated through distillation under vacuum (30-80 mm Hg). The obtained solid product was dried at 37° C. for 15 hours to further remove solvent residue, and the drying process was continued under vacuum at 35-40° C. for 8 hours to afford the amorphous form of indiplon as the product (4.6 g, yield 92%). The powder X-ray diffractogram of the product (FIG. 1) showed that the product was in amorphous form.

Method B: crystalline indiplon (3.0 g) and 14.0 g PEG 8000 was completely dissolved in 100 mL ethanol and dichloromethane (1:1, v/v) solvents under heating at 40° C., and further stirring the solution. The solvents were evaporated through distillation under vacuum (30-80 mm Hg) to obtain solid residue product. The obtained product was then grounded, and dried under vacuum at 45° C. for 15 hours, and the drying process was continued under vacuum at 35-40° C. for 8 hours to remove the solvent. The resulting substance (14.1 g) was solid amorphous dispersion of indiplon and PEG 8000.

Method C: crystalline indiplon (2.0 g) was dissolved in methanol (100 ml) under heating to 50° C. The hot solution was further heated to boiling point or under reflux. The solvent was evaporated through distillation under vacuum (30-80 mm Hg) to obtain solid product. The obtained product was then dried under vacuum at 42° C. for 15 hours to afford the amorphous from of indiplon (1.7 g, yield 85%). The powder X-ray diffractogram confirmed that the product was in amorphous form.

Method D: crystalline indiplon (2.0 g) was dissolved in n-propanol (160 ml) under heating to 40° C. The hot solution was further heated to boiling point or under reflux. The solvent was evaporated through distillation under vacuum (30-80 mm Hg) to obtain solid product. The obtained product was then dried under vacuum at 40° C. for 15 hours to afford the amorphous form of indiplon (1.8 g, yield 90%). The powder X-ray diffractogram confirmed that the resulting substance was in amorphous form.

Method E: crystalline indiplon (2.0 g) was dissolved in ethanol and dichloromethane (1:1, v/v) (80 ml) under heating to 40° C. The suspension mixture was then heated to boiling point or under reflux. The solvent was evaporated through distillation under vacuum (30-80 mm Hg) to obtain solid product. The obtained product was then dried under vacuum at 40° C. for 15 hours to afford the amorphous form of indiplon (1.8 g, yield 90%). The powder X-ray diffractogram of the product showed that the resulting substance was in amorphous form.

Example 2

Preparation of Solid Amorphous Dispersion of Indiplon and PVP: Spray Drying Method Method F: crystalline indiplon (6.0 g) and polyvinylpyrrolidone (PVP, K=30) (20.0 g) was dissolved in 200 ml of ethanol and acetone (1:1, v/v), and the suspension mixture is heated to 40-50° C. to obtain a clear solution. The hot solution was cooled to ambient temperature (25-30° C.), and then subjected to spray drying in a Mini-Spray Dryer (e.g., Buchi Model-190) at an inlet temperature 119-140° C. and outlet temperature 74-85° C. using nitrogen gas. A light-white powder of solid dispersion containing indiplon and PVP in an amorphous form was obtained. The product was further dried under vacuum at 45° C. for 15 hours to afford 22.5 g of the desired solid amorphous dispersion of indiplon and PVP.

Method G: crystalline indiplon (3.0 g) was dissolved in 150 mL of ethanol solvent, and the suspension is heated to 40-50° C. to obtain a clear solution. The suspension mixture was cooled to ambient temperature (25-30° C.), and then subjected to spray drying in a Mini-Spray Dryer (e.g., Buchi Model-190) at an inlet temperature 109-120° C. and outlet temperature 54-65° C. using nitrogen gas. A light-white powder of amorphous form of indiplon was obtained. The product was further dried under vacuum at 40° C. for 15 hours to afford 2.6 g of the desired product (yield, 87%). The powder X-ray diffractogram showed that the resulting substance was in amorphous form.

Method H: crystalline indiplon (10.0 g) was dissolved in 100 mL of acetone solvent under heating to 40° C. to obtain a clear solution. The suspension mixture was cooled to ambient temperature (25-30° C.), and then subjected to spray drying in a Mini-Spray Dryer (e.g., Buchi Model-190) at an inlet temperature 115-135° C. and outlet temperature 55-69° C. using nitrogen gas. The light-white powder of amorphous indiplon was obtained. The product was further dried under vacuum at 40° C. for 15 hours. The powder X-ray diffractogram showed that the resulting substance was in amorphous form.

Method I: crystalline indiplon (3.0 g) was dissolved in 200 mL of propanol solvent under heating to 40-50° C. to obtain a clear solution. The suspension mixture was cooled to ambient temperature (25-30° C.), and then subjected to spray drying in a Mini-Spray Dryer (e.g., Buchi Model-190) at an inlet temperature 115-135° C. and outlet temperature 55-65° C. using nitrogen gas. The light-white powder of amorphous form of indiplon was obtained. The product was further dried under vacuum at 40° C. for 15 hours. The powder X-ray diffractogram showed that the resulting substance was in amorphous form.

Method J: crystalline indiplon (3.0 g,) was dissolved in 200 mL of ethanol solvent under heating to 40-50° C. to obtain a clear solution. The suspension mixture was cooled to ambient temperature (25-30° C.), and then subjected to spray drying in a Mini-Spray Dryer (e.g., Buchi Model-190) at an inlet temperature 125-139° C. and outlet temperature 60-70° C. using nitrogen gas. A light-white powder of indiplon in an amorphous form was obtained. The product was further dried under vacuum at 45° C. for 15 hours. The powder X-ray diffractogram showed that the resulting substance was in amorphous form.

Example 3

Preparation of Pharmaceutical Composition Containing Amorphous Indiplon and Solid Amorphous Dispersion Pharmaceutical compositions for tablet dosage forms comprising amorphous indiplon or its solid amorphous dispersion and excipients are described in Table 1. Pharmaceutical compositions for capsule dosage forms comprising amorphous indiplon or its amorphous dispersion and excipients are shown in Table 2.

TABLE 1

Formulations A, B and C of 10 mg Indiplon Tablets

| Ingredients | mg/per tablet | | |
|---|---|---|---|
| | A | B | C |
| Core: | | | |
| Amorphous indiplon | 10 | — | 10 |
| Dispersion of indiplon and PVP (K30) | — | 44 | — |
| Mirocrystalline cellulose | 70 | 36 | 70 |
| Lactose anhydrous | 20 | — | 20 |
| Sodium starch glycolate | 51 | 51 | 47 |
| Pregelatinized starch | — | 20 | — |
| Sodium lauryl sulphate | 5 | 5 | 5 |
| Magnesium stearate | 3 | 3 | 3 |
| Coating | | | |
| Coating agent (HPMC)(sustained release) | — | — | 10 |
| Coating agent (opadry white), water* (Immediate release) | 6 | 6 | — |
| Total tablet weight (mg) | 165 | 165 | 165 |

*Evaporated during process

Table 1 lists three formulations of tablets: formulation A and B are for immediate release product, and formulation C is for sustained release product. Formulation B is for tablets comprising solid amorphous dispersion of indiplon and PVP. There are two major steps involved in manufacturing tablets (10 mg active ingredient): (1) preparation of indiplon tablet core; (2) coating the tablet core.

TABLE 2

Formulations A, B and C of 10 mg Indiplon Capsule

| Ingredients | mg/per capsule | | |
|---|---|---|---|
| | A | B | C |
| Core: | | | |
| Amorphous indiplon | 10 mg | — | 10 mg |
| Dispersion of indiplon and PEG 8000 | — | 56 | — |
| Mirocrystalline cellulose (avicel PH-101/102) | 70 | 36 | 70 |
| Lactose anhydrous | 20 | — | 20 |
| Sodium starch glycolate | 51 | 39 | 47 |
| Pregelatinized starch | — | 20 | — |
| Sodium lauryl sulphate | 5 | 5 | 5 |
| Magnesium stearate | 3 | 3 | 3 |
| Talc | 4 | 4 | 4 |
| Coating | | | |
| Coating agent (HPMC, E50/K50) | — | — | 10 |
| Total capsule weight (mg/capsule) | 160 | 160 | 166 |

For making tablets, the amorphous indiplon or the solid amorphous dispersion of indiplon and carrier are sifted by a clean screen (typically 0.066"), and other excipients are sifted by another screen (typically 0.080"). The sieved materials are then mixed in a tumbler at a speed of 100 rpm for 15 minutes, to afford completely homogeneous materials. The mixed materials are compressed into tablet cores using tablet-manufacturing equipments. The tablet cores are then placed on the tablet-coating machine, which is pre-heated to 60° C. for coating. Prior to spraying the coating agents, the coating pan's speed is adjusted to 5-9 rpm and the exhaustive temperature is maintained at 40-50° C. The coated tablets are dried for 5-10 minutes. The tablets are placed in the induction-sealed bottles with desiccants.

Table 2 lists three formulations of capsules. Formulation A and B are for immediate release capsules, and formulation C is for sustained release capsules. Formulation B comprises the solid amorphous dispersion of indiplon and PEG 8000. Following are procedures to make capsules. The active ingredient or solid amorphous dispersion of indiplon is sieved by a clean screen (typically 0.066"), and other excipients are sieved by another screen (typically 0.080"). The sieved materials are mixed in a tumbler at a speed of 100 rpm for 15 minutes. For preparing immediate release capsules, the mixed materials are directly inserted into the capsule shells. For sustained release capsules, the mixed materials are further converted into pellets, which are then coated with suitable coating agents. The obtained capsules are packaged in induction-sealed bottles with desiccants for storage.

We claim:

1. A solid amorphous N-Methyl-N-[3-[3-[2-thienylcarbonyl]pyrazolo[1,5-a]pyrimidin-7-yl]phenyl]acetamide (indiplon), characterized in that its X-ray powder diffraction pattern lacks discernible or sharp peaks.

2. The amorphous indiplon according to claim 1, comprising less than 5% crystalline indiplon other than polymorph Form III.

3. The amorphous indiplon according to claim 1, comprising less than 2% crystalline indiplon other than polymorph Form III.

4. The amorphous indiplon according to claim 1, comprising less than 0.5% or essentially free of crystalline indiplon.

5. A process for preparing amorphous N-Methyl-N-[3-[3-[2-thienylcarbonyl]pyrazolo[1,5-a]pyrimidin-7-yl]phenyl]acetamide (indiplon) by distillation, comprising the following steps:

a) dissolving indiplon starting material in dichloromethane, acetone, acetonitrile or a straight or branched chain $C_1$-$C_4$ alcohol solvent or mixtures thereof;

b) removing the solvent by distillation;

c) drying the product to afford the amorphous indiplon.

6. The process according to claim 5, wherein a straight or branched chain $C_1$-$C_4$ alcohol solvent is selected from the group consisting of methanol, ethanol, n-propanol, isopropanol or branched-chain butanols or mixtures thereof.

7. A process for preparing amorphous N-Methyl-N-[3-[3-[2-thienylcarbonyl]pyrazolo[1,5-a]pyrimidin-7-yl]phenyl]acetamide (indiplon) by spray drying, comprising the following steps:

a. dissolving the starting material indiplon in a solvent under heating;

b. removing the solvent by spray drying;

c. drying the product to obtain the amorphous form of indiplon.

8. The process according to claim 7, wherein the solvent is selected from the group consisting of methanol, ethanol, dichloromethane, acetone or mixtures thereof.

9. The process according to claim 5 or claim 7, wherein the drying temperature is 35-65° C.

10. A solid pharmaceutical composition comprising a therapeutically effective amount of amorphous indiplon and at least one pharmaceutical acceptable excipient.

11. The pharmaceutical composition according to claim 10, wherein amorphous indiplon is solid amorphous indiplon or solid amorphous dispersion of indiplon and a carrier.

12. The carrier according to claim 11 is selected from the group consisting of solid polyethylene glycol (PEG), polyvinylpyrrolidone (PVP), lactose, starches, mannitol, methylcellulose, hydroxymethylcellulose, ethylcellulose, hydroxyethylcellulose, hydroxypropylcellulose, hydroxypropylmethylcellulose (HPMC) or α-cyclodextrin, β-cyclodextrin or hydroxylpropyl-β-cyclodextrin.

13. The pharmaceutical composition according to claim 10, wherein the unit dosage form is tablets, capsules, powders, dispersion, pellets or suppositories.

* * * * *